United States Patent [19]

Wikström

[11] Patent Number: 4,784,652

[45] Date of Patent: Nov. 15, 1988

[54] EYEWASH DISPENSER

[75] Inventor: Jan Wikström, Fagersta, Sweden

[73] Assignee: Fagersta EL & Diesel AB, Fagersta, Sweden

[21] Appl. No.: 84,211

[22] Filed: Aug. 12, 1987

Related U.S. Application Data

[63] Continuation-in-part of Ser. No. 839,340, Mar. 13, 1986, abandoned.

[30] Foreign Application Priority Data

Mar. 27, 1985 [SE] Sweden ................................ 8501504

[51] Int. Cl.⁴ ............................................ A61M 35/00

[52] U.S. Cl. .................................. 604/295; 604/141; 604/148; 604/294; 604/310; 222/82; 222/386.5; 4/616; 4/620

[58] Field of Search ................ 604/131, 132, 140–149, 604/289–299, 310; 222/82, 96; 4/615–617, 620, 624

[56] References Cited

U.S. PATENT DOCUMENTS

| | | | |
|---|---|---|---|
| 3,022,785 | 2/1962 | Crockford et al. | 604/145 |
| 3,208,646 | 9/1965 | Wessenger | 222/386.5 |
| 3,420,418 | 1/1969 | Rousset et al. | 222/82 |
| 3,468,308 | 9/1969 | Bierman | 604/132 |
| 3,519,167 | 7/1970 | Rast | 222/386.5 |
| 3,662,929 | 5/1972 | Sims | 222/386.5 |
| 4,159,790 | 7/1979 | Bailey | 222/386.5 |
| 4,175,704 | 11/1979 | Cohen | 604/295 |
| 4,468,220 | 8/1984 | Willbanks | 604/145 |

FOREIGN PATENT DOCUMENTS

| | | | |
|---|---|---|---|
| 2747593 | 4/1979 | Fed. Rep. of Germany | 604/141 |
| 923977 | 4/1963 | United Kingdom | 604/297 |

*Primary Examiner*—C. Fred Rosenbaum
*Assistant Examiner*—Mario Costantino
*Attorney, Agent, or Firm*—Walter Ottesen

[57] ABSTRACT

The invention relates to a portable, handheld eyewash dispenser for discharging an eyewash liquid. The eyewash dispenser includes a housing and an expandable rubber bladder mounted in the housing. The housing and the rubber bladder conjointly define a chamber for accommodating the eyewash liquid therein. A propellant cartridge containing a propellant under pressure is mounted in the rubber bladder. A pressure valve responsive to a predetermined pressure of the eyewash liquid is mounted in the housing. A release mechanism is provided for acting on the propellant cartridge for discharging the propellant therefrom to inflate and expand the bladder thereby imparting pressure to the eyewash liquid causing the latter to be expressed through a nozzle. The housing is configured to permit the user to comfortably grasp the dispenser in one hand. The user can swing the eyewash dispenser with the hand so as to strike the release mechansim against a hard surface thereby actuating the latter and causing the eyewash liquid to be expressed through the nozzle.

3 Claims, 1 Drawing Sheet

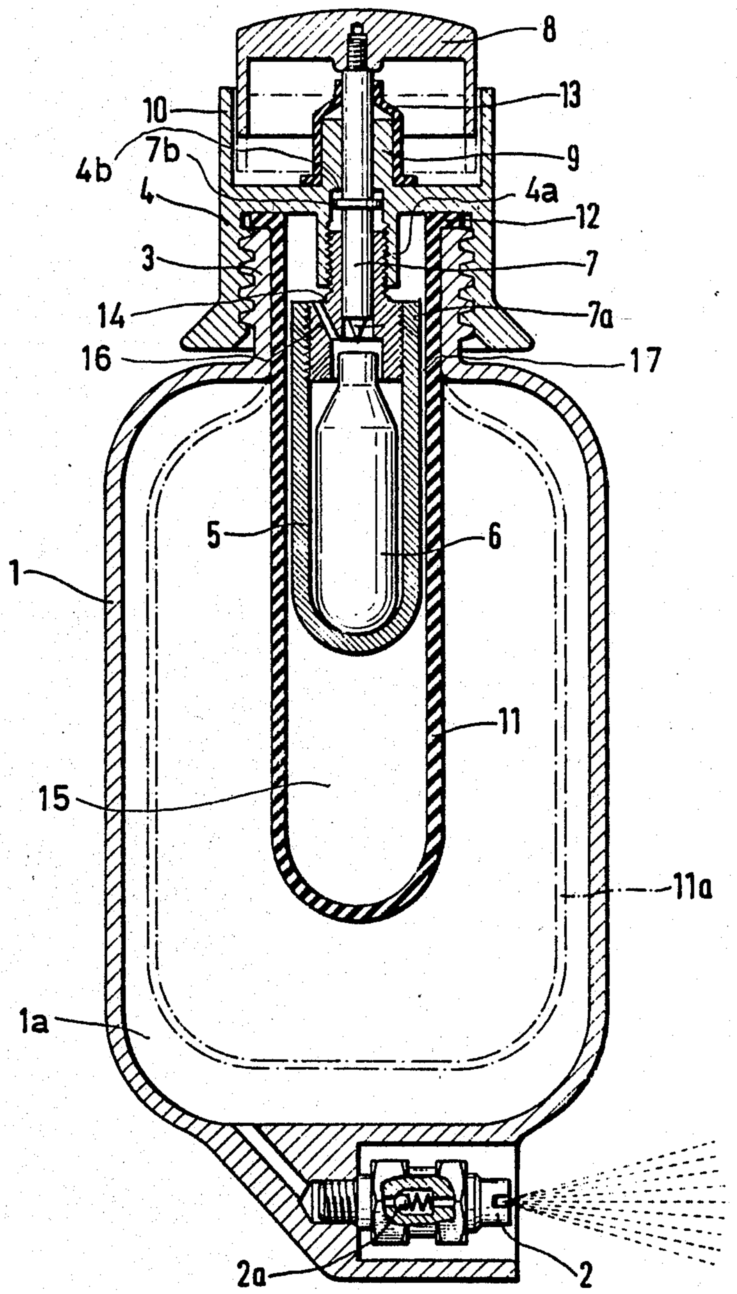
8
10
13
4b
7b
9
4
4a
12
3
7
14
7a
16
17
5
6
1
11
15
11a
1a
2a
2

EYEWASH DISPENSER

RELATED APPLICATION

This is a continuation-in-part of application Ser. No. 839,340, filed Mar. 13, 1986 and entitled "Eye Wash Station" now abandoned.

FIELD OF THE INVENTION

The invention relates to a handheld portable eyewash dispenser having a reservoir for liquid. The reservoir is equipped with a nozzle having a pressure valve through which the liquid is expressed in spray form under the influence of a propellant gas. The propellant gas is stored in a propellant cartridge disposed within the reservoir and is released by a release mechanism.

BACKGROUND OF THE INVENTION

U.S. Pat. No. 3,871,554 discloses an eyewash dispenser having a collapsible liquid container disposed in a fixed frame. A preloaded spring is disposed between the frame and the container. When the eyewash dispenser is to be used, the spring is released by means of a rod-like release mechanism. When using the eyewash dispenser disclosed in U.S. Pat. No. 3,871,554, the user holds a handle in the frame with one hand while he releases the spring with the other by pressing on the release rod. It is difficult for the user to release the spring without using both hands.

Eyewash dispensers are often used at workplaces where work is done with liquids which, if they come into contact with the eyes, can easily cause injury if the hazardous liquid is not quickly neutralized or removed. It is then essential that the eyewash dispenser that is intended to be used to prevent eye injury when an accident occurs should be readily accessible, easy to grip and easy to handle and can be made to discharge its contents by means of a simple motion.

It is also essential that the eyewash dispenser can be held and activated with only one hand so that the accident victim can hold the eyelid open with the other hand thereby permitting the neutralizing liquid to irrigate the eyes.

Another requirement that should be made on the eyewash dispenser is that the liquid is hygienically contained and can be expressed in spray form over an extended period of time and under constant pressure. The eyewash dispenser should also be configured so that it can be used without modification for different types of flushing liquid and so that spent parts of the eyewash dispenser are easy to replace.

SUMMARY OF THE INVENTION

It is an object of the invention to provide an eyewash dispenser which fulfills the requirements delineated above.

It is another object of the invention to provide an easy-to-handle eyewash dispenser that can be carried in one hand and which is equipped with a release mechanism that can be activated quickly and easily by means of the carrying hand alone.

It is still another object of the invention to provide an eyewash dispenser wherein the reservoir vessel is easy to grip and wherein the liquid can be expressed from the valve in spray form with full force over an extended period of time.

The portable, handheld eyewash dispenser of the invention is for discharging an eyewash liquid. The eyewash dispenser includes: a housing; resilient means mounted in the housing to conjointly define a reservoir chamber therewith for holding the eyewash liquid therein; pressure valve means responsive to a predetermined pressure of the eyewash liquid for releasing the same to the ambient; nozzle means for guiding the eyewash liquid to the ambient; and, pressure supply means for expanding the resilient means to reduce the volume of the chamber thereby pressurizing the eyewash liquid and expressing the same through the nozzle means to the ambient.

BRIEF DESCRIPTION OF THE DRAWING

The invention will now be described with reference to the drawing which shows a side elevation view, partially in section, of an embodiment of the eyewash dispenser according to the invention.

DESCRIPTION OF THE PREFERRED EMBODIMENTS OF THE INVENTION

The eyewash dispenser includes a vessel 1 for the liquid that is intended to be used to prevent eye injury. The vessel 1 is cylindrical in shape and of such a size that it can easily be gripped and held with one hand. A bladder 11 is mounted in the vessel 1 and conjointly defines a reservoir 1*a* therewith for holding an eyewash liquid such as water. The vessel 1 is sealed at one end and fitted at this one end with a nozzle 2 through which the liquid in the reservoir 1*a* is intended to be expressed in spray form when acted on by a propellant, for example compressed air. Reference numeral 2*a* identifies a check valve inside the nozzle 2.

At its other end, the vessel 1 is open and provided with an externally threaded neck 3 for threadably engaging a sleeve-shaped cap 4. The cap 4 has a downwardly extending cylindrical portion 4*a* in which a connecting piece 14 is threadably engaged. A holder 5 for accommodating a propellant cartridge 6 is threadably attached to connecting piece 14 so as to be centrally mounted in the cap 4. With the holder 5 mounted on connecting piece 14 as shown, the holder projects downwardly and is disposed within bladder 11 when the cap 4 is threadably engaged with neck 3. The cartridge holder 5 is tubular for accommodating a propellant cartridge 6 therein. Connecting piece 14 encloses a striking pin 7 projecting through the cap 4 in whose upper, outer end a release button 8 is attached. At its lower, inner end, the striking pin 7 has a point 7*a* facing downwardly toward the propellant cartridge 6.

The cap 4 is provided on the top with a centrally located sleeve 9 through which the striking pin 7 projects above the cap 4. The edges 10 of the cap 4 are raised to form a cylindrical recess in which the release button 8 is mounted.

After the striking pin 7 has struck and penetrated the upper end of the cartridge 6, the propellant is released and passes under pressure into the enclosed space 15 through a passage 16 formed in connecting piece 14.

The gas contained in the cartridge 6 does not, when it is discharged, come into direct contact with the liquid in the reservoir 1*a*. This is prevented by the oblong cylindrical bladder 11 that surrounds the holder 5 in spaced relationship thereto. In this way, the bladder 11 and holder 5 conjointly define an annular space 17 through which the propellant gas can pass into the space 15 of the bladder 11 after leaving passage 16.

The bladder 11 is made of elastic material such as rubber and is closed off at the bottom end thereof. The bladder 11 is open at its upper end where it is provided with a flange 12 which lies flush against the upper edge of the neck 3 against which it tightly seals when the cap 4 is screwed onto the neck 3 and the rubber bladder is inserted into the vessel 1. In this way, the liquid in the vessel 1 is prevented from leaking out between the cap 4 and the neck 3.

The striking pin 7 is disposed to slide within connecting piece 14 and sleeve 9 which guide its axial movement. The sleeve 9 projects vertically upwardly on top of the cap 4. In order to prevent gas from escaping from the sleeve 9, an elastic, collar-shaped seal 13 is arranged so that it encloses the sleeve 9 and the upper portion of the striking pin 7.

The eyewash dispenser is used in situations where the user has accidentally gotten hazardous liquid in the eyes. The victim is partially paralyzed and gropes more or less blindly for the eyewash dispenser which should be mounted at a designated place. The user grips the eyewash dispenser with one hand, strikes or pushes the end of the vessel 1 where the release button 8 is located against the knee or a hard surface so that the striking pin attached to the release button 8 strikes the cartridge 6 with its point 7*a* thereby causing the propellant gas to be released under pressure into the rubber bladder 11 via passage 16 and annular space 17 whereupon the bladder 11 expands to the position 11*a* shown in phantom outline. This pressurizes the liquid in the reservoir 1*a* and causes the same to be expressed through the nozzle 2.

At the same time as the cartridge 6 is discharged, the striking pin 7 is acted upon by pressure from below, which, against the spring force in the elastic seal 13, lifts the striking pin 7 and thereby the release button 8 to a higher level than that of its original starting position, thereby indicating that the eyewash is released. Specifically, in addition to expanding the bladder 11 as described above, the propellant gas released from the cartridge 6 also pushes the striking pin 7 upwardly until flange 7*b* comes into abutment with seat 4*b* at the bottom of cylindrical portion 4*a*.

It is understood that the foregoing description is that of the preferred embodiments of the invention and that various changes and modifications may be made thereto without departing from the spirit and scope of the invention as defined in the appended claims.

What is claimed is:

1. A portable, hand-held eyewash dispenser for discharging an eyewash liquid, the eyewash dispenser comprising:

a housing having a wall inner surface and being configured to permit the user to comfortably grasp and hold the same in one hand;

an expandable bladder having an outer surface and disposed in the interior of said housing;

said inner and outer surfaces conjointly defining a reservoir chamber therebetween for holding the eyewash liquid;

a propellant cartridge containing a propellant fluid under pressure;

a holder mounted within said bladder for holding said propellant cartridge therein;

nozzle means communicating with said reservoir chamber for guiding the eyewash liquid to the outside;

manually-actuated release means mounted on said housing for penetrating said cartridge to release said propellant fluid;

passage means interconnecting said cartridge and said bladder for conducting the released fluid into the interior of said bladder for filling and expanding the latter thereby placing the eyewash liquid under a predetermined pressure; and, pressure valve means, mounted in said nozzle means, responsive to said predetermined pressure of said eyewash liquid for releasing the same to the outside.

2. The portable, hand-held eyewash dispenser of claim 1, said manually-actuated release means comprising: a striking pin mounted on said housing and above said cartridge for movement between a first position whereat said pin is clear of said propellant cartridge and a second position whereat said pin penetrates said cartridge for releasing the propellant fluid contained therein; and, a manually actuable button mounted on said striking pin for actuating said pin in response to a manually imparted blow for displacing the pin from said first position to said second position.

3. A portable, hand-held eyewash dispenser for discharging an eyewash liquid under the pressure of a fluid propellant contained in a propellant cartridge, the eyewash dispenser comprising:

a housing having a wall inner surface and being configured to permit the user to comfortably grasp and hold the same in one hand;

an expandable bladder having an outer surface and disposed in the interior of said housing;

said inner and outer surfaces conjointly defining a reservoir chamber therebetween for holding the eyewash liquid;

a holder mounted within said bladder and having an interior adapted to accommodate the propellant cartridge therein;

nozzle means communicating with said reservoir chamber for guiding the eyewash liquid to the outside;

manually-actuated release means mounted on said housing for penetrating the cartridge to release said propellant fluid;

passage means extending between said interior of said holder and said bladder for conducting the released fluid into the interior of said bladder for filling and expanding the latter thereby placing the eyewash liquid under a predetermined pressure; and, pressure valve means, mounted in said nozzle means, responsive to said predetermined pressure of said eyewash liquid for releasing the same to the outside.

* * * * *